United States Patent [19]
Teeple, Jr.

[11] Patent Number: 5,151,095
[45] Date of Patent: Sep. 29, 1992

[54] LASER SHIELD WITH INDICATOR MEANS

[76] Inventor: Edward Teeple, Jr., 641 Ridgefield Ave., Pittsburgh, Pa. 15216

[21] Appl. No.: 440,665

[22] Filed: Nov. 22, 1989

[51] Int. Cl.$^5$ .............................................. A61B 17/36
[52] U.S. Cl. ........................................ 606/2; 128/849; 128/858; 219/121.6; 340/557; 340/600
[58] Field of Search ...................... 219/121.85, 121.82, 219/121.61, 121.63, 121.64, 121.6; 340/557, 600; 128/849, 858; 606/2

[56] References Cited

U.S. PATENT DOCUMENTS

| | | | |
|---|---|---|---|
| 2,405,515 | 8/1946 | Neyzi | 338/334 X |
| 4,901,738 | 2/1990 | Brink et al. | 606/2 X |
| 4,917,481 | 4/1990 | Koechner | 350/363 |

Primary Examiner—C. L. Albritton
Attorney, Agent, or Firm—Reed Smith Shaw & McClay

[57] ABSTRACT

A flexible laser shield for use during procedures in which lasers are utilized, which has an insulating layer positioned under a metallic layer and covered by an exterior opaque layer to inhibit the refleting of ambient room light during use. A second metallic layer, also optionally covered by a flexible, opaque material may be added to provide additional protection and make the shield reversible. The exterior opaque, metallic and insulating layer are attached together at their adjacent surfaces or at their peripheries. The laser shield may also utilize visual, audible, vaporous and/or electrical warning or alarm systems, and may embody the use of a variety of insulating materials to protect personnel and equipment from damage caused by laser radiation.

15 Claims, 5 Drawing Sheets

LASER SHIELD WITH INDICATOR MEANS

FIELD OF THE INVENTION

The present invention relates to a laser shield and, in particular, to a layered, flexible metallic insulated shield useful in protecting personnel and equipment from injury or damage that can be caused by laser radiation, and in detecting and alerting personnel of the harmful presence of that radiation. More specifically, surgical patients and operating room personnel require protection during surgical procedures involving lasers, and in protecting operating room equipment including anesthesia circuits from exposure to laser radiation.

BACKGROUND OF THE INVENTION

It is becoming more common to use lasers to perform various surgical procedures, research functions, industrial processes, and similar techniques. It is well-known that the radiation from such lasers must be confined to the operative area, and that the lasers used under a variety of circumstances pose a danger to personnel and equipment. It is equally well-known that it is difficult, if not at times impossible, to prevent the occurrence of stray radiation in such situations.

In particular, surgical operating room personnel have begun wearing protective eyeglasses, and patients undergoing laser operative procedures have been provided moistened gauze over the eyes. More recently, a surgical eye mask has been developed to protect patients during laser surgery. (See U.S. Pat. No. 4,635,625.) Surgical shields or blankets have also been developed to protect operating room patients, personnel and equipment. (See U.S. Pat. Nos. 4,616,641 and 4,715,366.) A laser-resistant backup pad (U.S. Pat. No. 4,520,814), and a ceramic dish (West German Patent No. 2,207,387) have also been developed to protect operating room patients during laser surgery.

The need for detection of the presence of errant or stray radiation, as well as a means to prevent harm to personnel and equipment during laser-use operations without surgery degrading the efficiency of the operating environment has become apparent. Importantly, personnel utilizing lasers need a means to quickly and effectively alert them of the presence of stray radiant energy that may injure personnel and equipment in their work environments. Further, under the intense, bright ambient lighting conditions that must exist in surgical operating rooms, it is difficult to detect the presence of stray radiation unless that radiation results in pain or is otherwise noticed by a conscious occupant of the operating room when existing shields that may or may not provide adequate protection are used. Present day eye, personnel and equipment shields are comprised of a highly reflective, aluminized, albeit matte, surface or finish. These shields may in many situations degrade the efficiency of the laser operating environment by reflecting ambient light into the eyes of the personnel working in that environment.

Personnel may be injured by direct exposure to a laser beam on the skin, causing burns or flesh wounds, or, in some situations, opthalmic injury or loss of vision can result if the eyes were to become accidentally exposed. In particular, operating room patients are highly at risk when anesthetized, particularly when a patient is under general anesthesia), since the patient is unaware of or otherwise unable to alert the surgical personnel of the occurrence of an injury or dangerous condition.

The use of wet towels to protect against stray laser energy is not a satisfactory method because the sterile plastic sheet below the towels can be ignited by the laser beam. Furthermore, bacterial contamination may occur when plastic sheets are not used to protect the patient. There is a potential of fire from towels which have not been remoistened during the operative procedure. As such, wet towels and other similar methods in no way served to effectively warn personnel of the presence of stray laser radiation until after injury may have occurred.

The potential laser hazards encountered by patients are also encountered by the operating room personnel. Although operating room personnel can, to some extent, avoid continued contact from the beam by stepping out of its path or by alerting the user, it is not always possible for personnel to be aware of and to then remove themselves from the path of the laser beam. In many cases, it is difficult to identify a potentially dangerous stray laser radiation problem until after injury has occurred. Even short exposures may cause injury, provided operating personnel discover in time that a dangerous stray laser radiation condition exists.

Another problem encountered is the exposure of the operating room equipment such as anesthesia machines and circuits to undetected laser radiation. Anesthesia circuits often must be positioned near the operative field, especially during neurosurgery or during facial or oral surgery. Typically, these circuits have been wrapped in aluminum foil to deflect the stray radiation. However, such wrapping prevents the anesthesiologist from observing these circuits. Aluminum foil is very difficult to work with, especially around the endotracheal tube, and often fails to provide sufficient protection to equipment.

Another problem encountered with other laser shields is the undesirable conditions that these reflective shields, drapes and eye masks create in the operating room due to their tendency to reflect the high-intensity lights in operating rooms so as to distract and otherwise impair the vision of operating room personnel. A need for a laser warning and protective system that becomes effective only once an actual dangerous stray laser radiation condition is present in the operating room has become apparent. The highly reflective surface of present day shields, although needed to protect against the harms caused by stray radiation once that radiation is actually encountered, has the effect of lowering the efficiency of laser operating personnel whose vision is impaired by the very qualities that make such shields effective against laser radiation.

The same problems that occur in surgical laser applications may also occur when lasers are used for research, industrial, and a variety of other purposes; personnel can risk serious injury and equipment may be damaged when errant laser radiation remains undetected or unprotected against.

It would be desirable, therefore, to provide a laser-shield warning system alerting personnel who utilize lasers by visual, audible and odor or vapor alarm means of the presence of stray laser radiation and which records the path and presence of that radiation, and at the same time protects patients, personnel, and equipment from damage caused by lasers. It is also an objective of the present invention to improve the ability of laser shields to thermally insulate personnel and equipment against undesired exposure to laser energy using even more compact and lightweight, yet highly protective laser shields. It is a also an objective of the invention to provide a laser shield that does not reflect the intense ambient light of the operating room/laser use facility so as to distract or impair the vision of laser operators in the performance of their tasks.

SUMMARY OF THE INVENTION

Generally, the present invention provides personnel and equipment shields which are comprised of a flexible opaque exterior layer (preferably black or other acceptable non-reflective color), an underlying flexible, protective metallic layer (preferably of an aluminized foil) followed by a flexible insulating layer which may be comprised of a number of materials. The shield may be further comprised of a second metallic layer on the opposite side of the insulating layer and a second flexible opaque exterior layer. The second metallic layer increases the protection provided by the shield, and when coupled with the second opaque exterior layer, allows either side of the shield to be utilized to protect against laser radiation with equal effectiveness.

In one embodiment, a woven textile fabric inner layer, such as cotton gauze may be used to form the insulating layer. Other materials including nonwoven fabrics such as polypropylene glycol may be usefully substituted for less durable textile fabrics when desired. The outer periphery of the layers is fastened together to interpose the insulating gauze layer between the outer layers so as to form the blanket. Eyelets may be positioned along one or more edges or outer portions of the periphery so that the shield can be hung or otherwise affixed to personnel, equipment or other locations so as to partially isolate potentially harmful laser radiation.

In another embodiment of the invention, the shield may be constructed with concentric pre-cut or perforated openings which, in the case of surgical procedures, affording access to the operative field while protecting the bodies of patients and personnel. Any configuration or design of perforation can be used, but concentric circles or ellipses are most desirable for the typical laser operation. In this embodiment, it may also be desirable to provide an adhesive coating on one side of the blanket to prevent movement on the patient's body.

The above-described shields can be utilized for protecting equipment, including anesthesia circuits. It is often desirable to form the blanket or shield with a self-adhesive hook and loop fastener type material on the ends of fastening straps and/or along the outer edges of the shield to allow the shield to snugly fit and be held in position on personnel and equipment. It is often desirable to wrap the shield in a "c"-configuration and to provide either fixed or removable straps to provide ready access to view the protected area. These and other advantages of the present invention will become apparent from a review of the detailed descriptions of presently preferred embodiments of the invention taken in connection with the accompanying drawings.

In another embodiment, the present invention provides an eye mask shaped and contoured to cover the patient's eyes, the area above a patient's eyebrows, bridge of the nose and cheekbones, as well as the periphery of the mask to include the facial skin of the patient. The seal precludes the ingress of divergent laser radiation. In one specific embodiment, the outer layer and metallic layer is affixed to an insulating layer comprised of a pair of adsorptive pads, such as cotton or cotton gauze, which contain or are adapted to contain a moistening fluid, such as a saline solution to maintain the eye moisture during surgery or other laser procedures.

Positioned under the insulating adsorptive eye pads is a waterproof material, such as waxed paper, when it is desired to pre-moisten the mask. In such case, the moisture-proof material encompasses the entire adsorptive material and includes an adhesive perimeter to seal and secure it to the inner surface of the metallic layer of the eye shield, to keep the moisture in the adsorptive material from evaporating. Preferably, a backing material is positioned over the entire back of the eye mask. It is desirable that the backing be made of a material which is can be easily stripped from the adhesive on the periphery of the mask, such as a resin-coated paper. The backing material affords protection to the mask in its unused state. It is also possible to use a front protective sheet to protect the metallic layer of the mask. When the mask of this embodiment is desired for use, the backing is removed from the mask as well as the waterproof material over the adsorptive pads. The mask is then positioned over the eyes of the patient and the periphery of the mask pressed against the skin to create a seal.

In another embodiment at the present invention, the insulating layer of the surgical shield is treated with a material that will cause expansion or the forming of a "bubble" of the overlying aluminized sheets when the outer surface of the shield is exposed to laser radiation. This layer provides several important advantages over present day shields to include additional personnel and equipment insulation and protection, in the form of a cost-effective, light weight compact shield. The heat caused by laser radiation can cause damage to human tissue as well as operating room equipment and instruments. For example, plastic or other low melting point operating room equipment, as well as human tissue have a low tolerance for the heat generated by lasers. This embodiment functions to provide additional protection by displacing the exposed, heated metallic layer from the surface being protected by increasing the insulating ability of the previously deflated shield, and by dissipating the heat created by laser impingement on the metallic layer.

Alternatively, the shield can be comprised of an opaque exterior layer that functions via a variety of means to alert personnel when one of the protective integrity of the shield is compromised. Variations on this embodiment include:

(a) A laser/heat-sensitive opaque exterior layer that changes color when contacted by laser radiation.

(b) A laser/heat-sensitive opaque exterior layer that forms "bubbles" or that inflates on the surface of the shield so as to provide physical indicator that the shield has been subjected to laser energy that can be observed or felt by personnel as a result of the deformity caused by the inflation of heated region of the shield.

(c) A laser/heat-sensitive opaque exterior layer comprised of an odorous and/or vapor-releasing indicator material that alerts personnel or electrical sensors that the protective integrity of the shield has been damaged and that the shield should be replaced.

In another embodiment, the shield can be further equipped with a variety of specialized insulating layers, which function to prevent the heat that results from laser contact with the metallized layer from causing injury to personnel or damage to equipment and/or to warn personnel of the presence of errant laser radiation. In this embodiment, a honeycomb-type structured insulating layers function to protect and warn personnel and equipment in several ways, to include:

a) An insulating system that displaces the heat reflecting metallized layer of the shield away from the surface to be protected. (The thickness of the backing and its insulating properties can be varied according to the heat sensitivity of the items being protected and the intensity of the lasers being used.)

b) An audible warning system; when the honeycomb structure filled and sealed with air or other desirable gas inside is heated via heat transferred from the shield's metallized layer, the result and heat-related expansion of the enclosed material causes the pocket to expand and pop, giving off a distinctive sound when the shield is subjected to laser energy.

c) A vaporous warning system, in that once the pockets of gas, liquid, solid or combination thereof are breached due to heat expansion, a detectable vapor or odor is released so that according to the desired application, the vapor can be detected by the human sense of smell and/or by vapor detector instrument.

d) An electrical warning system; once the honeycomb pockets of electrically conductive liquid or gas pockets are heated the point that one or more burst so as to release that liquid, the liquid alters the current-resistive properties existing between a shield equipped with two metallized layers integrated throughout the shield; when the liquid between the "sandwiched" structure of the shield is released an electrical alarm is activated. In addition, when the shield is punctured, damaged, or otherwise physically breached, the electrical alarm would also sound.

An electrical alarm or detector device for this and other embodiments may be centrally or remotely located and connected to the shield via wires, and can service a plurality of shields in use. The alarm preferably is equipped with an visible indicator light, audible alarm and/or other test means to indicate proper functioning of the shield. When activated by exposure to laser radiation, the alarm can emit audible, visual and-/or other warning means to personnel, and can be connected to an interlock switch so as to automatically shut off or move the laser beam should a dangerous condition occur.

In another embodiment, the inner layers of the shield can be comprised of a material that will turn from a solid to a liquid or from a liquid to a gas, so as to permit the surrounding aluminized layers to contact each other, thereby altering the resistive or conductive conditions existing between the aluminized layers that can be detected by an alarm device. The detection device associated with this embodiment itself can be permanently or temporarily mounted on the shield so as to contact the aluminized surfaces of the shield and detect the above-described changes in conductivity or resistance. In this embodiment, a second or third insulating layer can be added so as to provide "levels" of protection against high-powered lasers. The additional insulating layers of the shield can be equipped so as to react under increased heat tolerances, so as to set off subsequent alarms indicating continued or increased danger of harm to the personnel or equipment being protected. Alternatively, the insulating layer of the shield can alternatively be comprised of a chemical that when heated by laser energy or other heat source, changes the resistance between the aluminized layers so as to set off an electrical alarm device, without the need for physical contact between the aluminized outer layers.

In another embodiment, a wire can be embedded in a continuous strand throughout the inner sheet material that will expand when contacted by laser or other heat source. When the material expands, the inelastic wire is severed, and the flow of electrical current and thereby activating an electrical warning means. The continuous strand of wire can alternatively be comprised of a material that will melt when the shield is subjected to laser energy, thereby breaking the circuit or changing the resistance in the circuit so as to set off an electrical alarm device.

Other advantages of the invention will become apparent from a perusal of the following detailed descriptions of presently preferred embodiments, and as show in connection with the accompanying drawings.

DESCRIPTION OF THE PRESENTLY PREFERRED EMBODIMENTS

Figure 1:
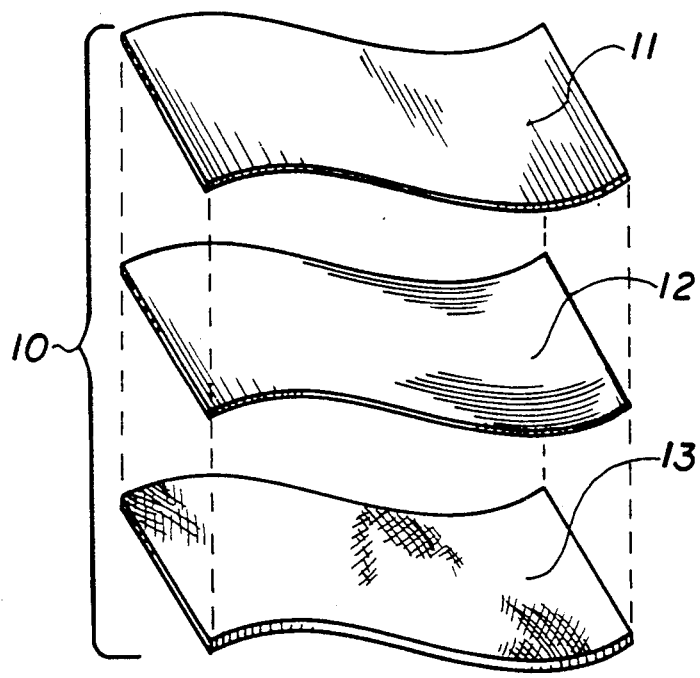
FIG. 1 is an exploded side elevation of the present invention which embodies an opaque layer, an underlying metallic layer and an insulating layer.

Referring to FIG. 1, laser shield 10 of the present invention is shown. The shield comprises a flexible external opaque layer 11, preferably 0.5 mm to 3 mm thick and with properties so that it alerts and protects laser-utilizing personnel and their equipment through one or more specialized properties of the presence of stray or errant laser radiation.

The exterior opaque layer may serve as a visual alarm for errant laser radiation, in that the exterior opaque layer emits a "puff" or "cloud" of non-toxic smoke when it is contacted by laser radiation. The shield may also embody the use of an audible alarm or warning system, in that the exterior opaque layer may be comprised of a material that when subjected to the heat of laser energy chemically reacts so as to give off snapping, sizzling or popping sound that will alert nearby, personnel to the presence of laser energy. The exterior opaque layer may also be comprised of a material that will form one or more bubbles when exposed to laser radiation so as to warn personnel.

The exterior opaque layer may also be comprised of a material that deteriorates or melts away to reveal the high reflective aluminized layer beneath it, so as to provide a sustained indicator that will alert operating room personnel of the presence of stray laser radiation, and record the path of that radiation. The exterior opaque layer may also be comprised of a material that will cause it act as a vapor or odor alarm, in that the outer opaque layer will emit a non-toxic vapor, odor or puff of smoke when subjected to laser energy, and is thereby recognized by human or other means to alert laser operating personnel of a dangerous stray laser radiation condition.

Further, the exterior opaque layer may also provide protection in that it does not reflect ambient room light, and that once the opaque layer is exposed to laser radiation, it partially burns or melts away (without igniting) to reveal the underlying highly reflective aluminized layer which then acts to effectively protect personnel and equipment from injury or damage by reflecting and dispersing potentially harmful laser radiation.

The thickness of the flexible opaque layer can be varied according to desired laser radiation exposure tolerances. The composition of the layer can also be varied according to the desired heat resistance, melting reaction process, scent or odor-producing characteristics, as well as other factors and desired performance characteristics.

The laser shield further comprises (as shown in FIG. 1), a metallic layer (12). This metallic layer preferably consists of aluminum foil having a thickness of approximately 3 mils. The thickness of the metallic layer is not critical, but it is to be understood that if the metallic layer is too thin it is subject to being easily damaged during use. On the other hand, if the metallic layer is exceptionally heavy, it becomes unwieldy and unmanageable on the operating table or on the patient. The foil normally will have a matte finish, as in many applications, a matte finish is preferable for reflected laser radiation beam dispersion.

Adjacent to metallized layer (12) in FIG. 1 is insulating layer (13). The insulating layer may be comprised of cotton gauze, polypropylene glycol or any similar sterilizable, pliable material, such as nonwoven sheets composed of elastomeric materials, to include pliable polyolefin or isotactic polypropylene. Typically, the insulating layer has a thickness of about one mil, so it conforms readily to manipulation of its contour by the surrounding metallic foil. If the foil is too thin, it will tend toward heat deforming; and, if excessively heavy, it will tend toward cracking with handling. For example, under actual testing with surgical lasers, the above-described insulating layer has been shown to resist to melting or ignition with flame within power limits used for clinical laser surgery.

High-density polyethylene, and copolymers of polypropylene and polyethylene, may also be usefully employed as the insulating layer. The most important prerequisite is that the polyolefin (preferably in thicknesses up to a few mils) must be drapable and hand moldable, while at the same time retaining its conformation shape during the normal range of temperatures created on the sheet surface by laser beam impingement. Shield 10 can be used to protect equipment, such as anesthesia circuits, and to protect personnel (to include anesthetized patients) against laser radiation.

Figure 2:
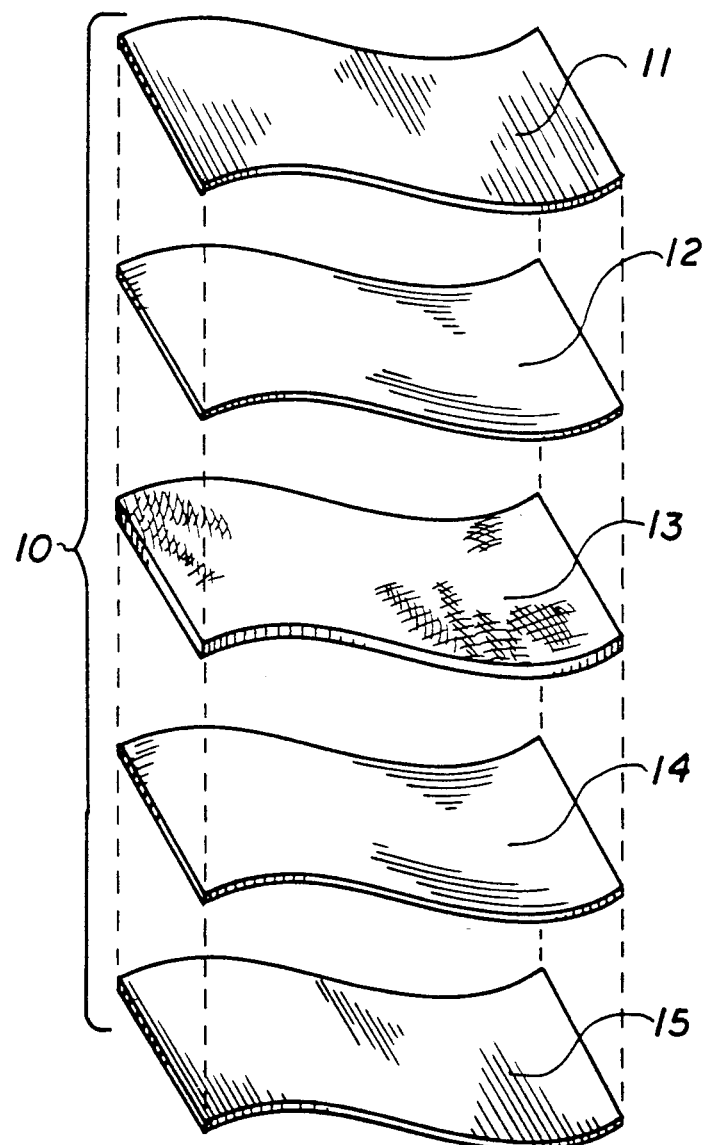
FIG. 2 is an exploded side elevation of a second embodiment of the present invention which embodies a second underlying metallic layer and a second opaque layer.

FIG. 2 shows a laser shield 10 which in addition to the opaque layer 11, metallized layer 12 and insulating layer 13 described in FIG. 1 further comprises a second metallized layer 14 positioned on the other side of the insulating layer from the first metallized layer 12, and, optionally, a second opaque layer 15 applied to the exterior surface of the second metallized layer 14. Like opaque layer 11, the thickness of opaque layer 15 can also be varied according to desired laser radiation exposure tolerances, and made of a variable composition according to the desired heat resistance, melting reaction process, scent or odor-producing characteristics and other factors. Metallized layer 14 is preferably formed from aluminum foil having the same thickness (approximately 3 mils) as metallized layer 12. Shield 10 as shown in FIG. 2 provides additional personnel and equipment protection due to the additional layers over the protection provided by shield 10 as shown in FIG. 1, and is also reversible in that either side of the shield can be used to safeguard against laser damage with equal effectiveness.

A number of variations on the design and function of insulating layer 13 are also useful in protecting personnel and equipment against the potential hazards of laser radiation. These embodiments are shown in FIGS. 3A through 3D.

Figure 3A:
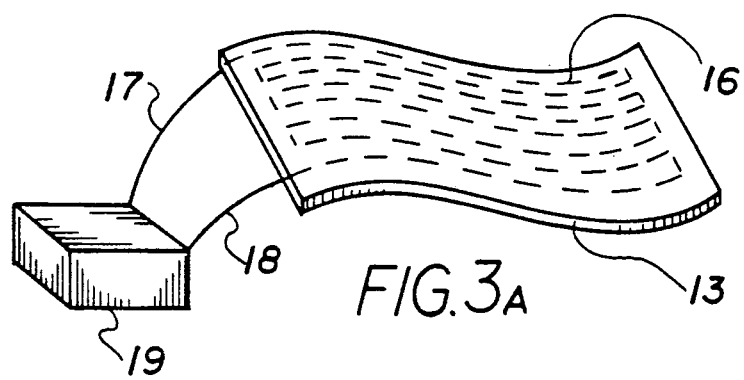
FIGS. 3A through 3D show four variations on the insulation layer of the laser shield.

FIG. 3A shows insulating layer 13 with an internal structure of continuous wire 16 that decomposes when exposed to laser radiation and heat, thereby breaking the circuit and setting off electrical alarm device 19 via connecting lead wires 17 and 18. Layer 13 as shown in FIG. 3A can also be used in place of layer 11 as shown in FIGS. 1 and 2, thereby serving both as the exterior flexible opaque layer and as a laser exposure warning device.

Figure 3B:
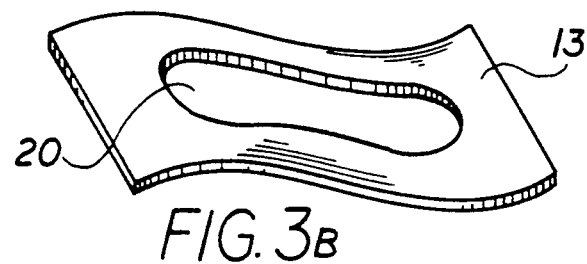
Figure 4:
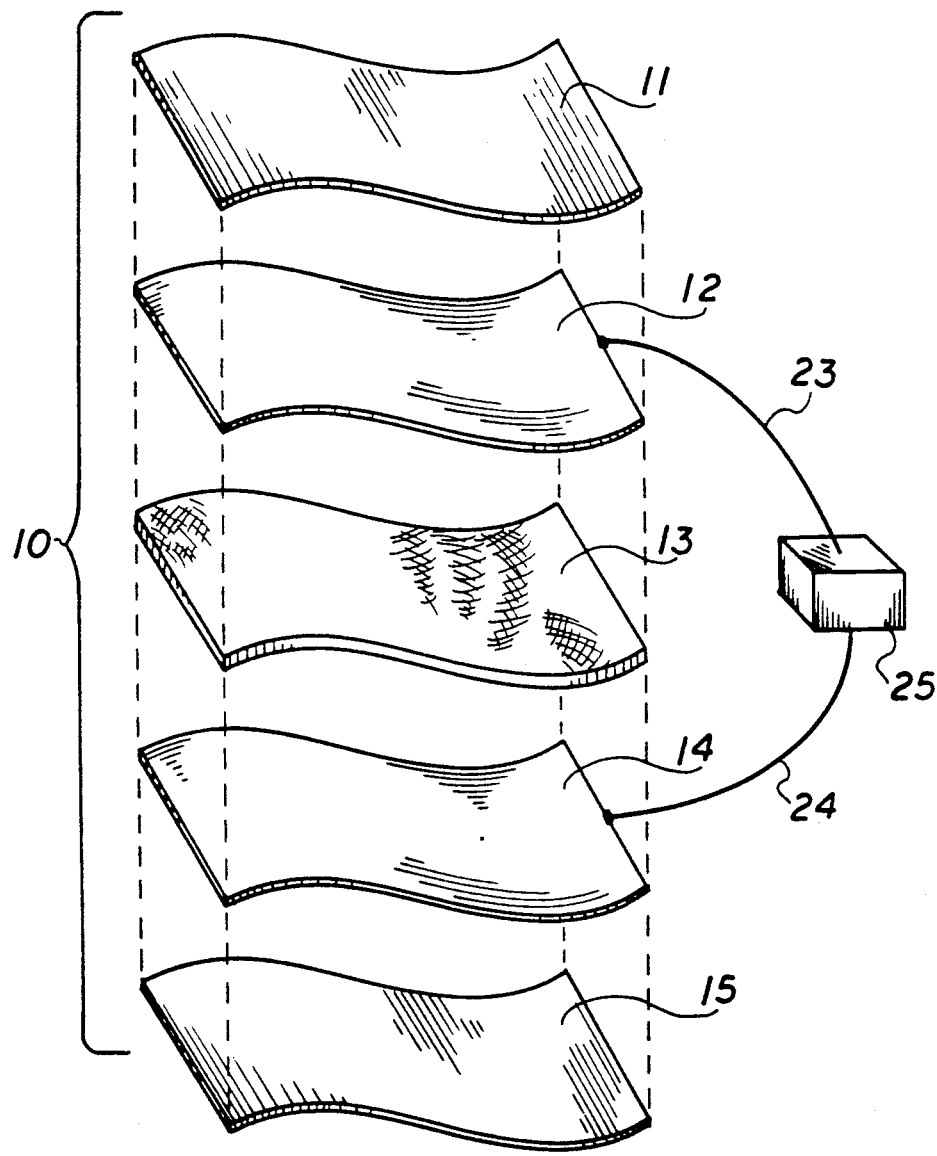
FIG. 4 is an exploded elevation of a shield that is comprised of an insulating layer that changes resistive properties when exposed to laser radiation.

FIG. 3B shows insulating layer 13 which comprises an internal structure of material that when subjected to laser radiation melts away to form hole 20; this embodiment is useful in shield 10 as shown in FIG. 4, to permit metallic layers 12 and 14 as shown in FIG. 4 to contact each other, thereby setting off electrical alarm device 25 via connecting lead wires 23 and 24.

Figure 3C:
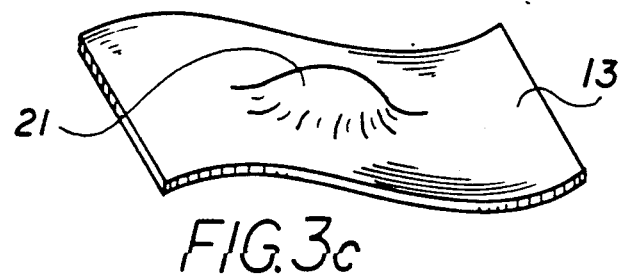

FIG. 3C shows insulating layer 13 comprising an internal structure of material that when subjected to laser radiation expands to form bubble 21 this embodiment may also include a surface structure of continuous wire as shown in FIG. 3A, which when expanded, acts to sever wire 16 so as to set off alarm 19.

Figure 3D:
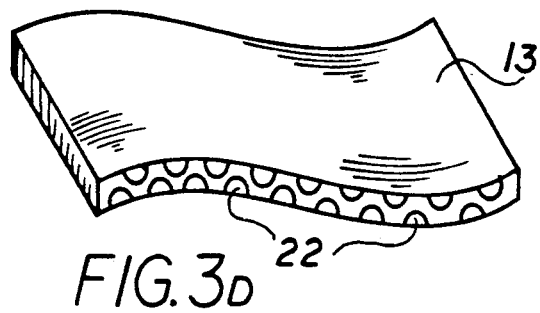

FIG. 3D shows insulating layer 13 which comprises an internal honeycomb-structure of pockets 22 filled with a gas or liquid; this embodiment is also useful in shield 10 as shown in FIG. 4, by changing the resistive properties existing between metallic layers 12 and 14 as shown in FIG. 4, thereby setting off electrical alarm device 25 via connecting lead wires 23 and 24.

FIG. 4 shows another embodiment of shield 10 as comprising an insulating layer 13 that changes resistive properties (chemically, or by heat-induced displacement), when exposed to laser radiation, which can subsequently be detected by an alarm device 25 attached to the metallic layers of the shield as described above.

Figure 5:
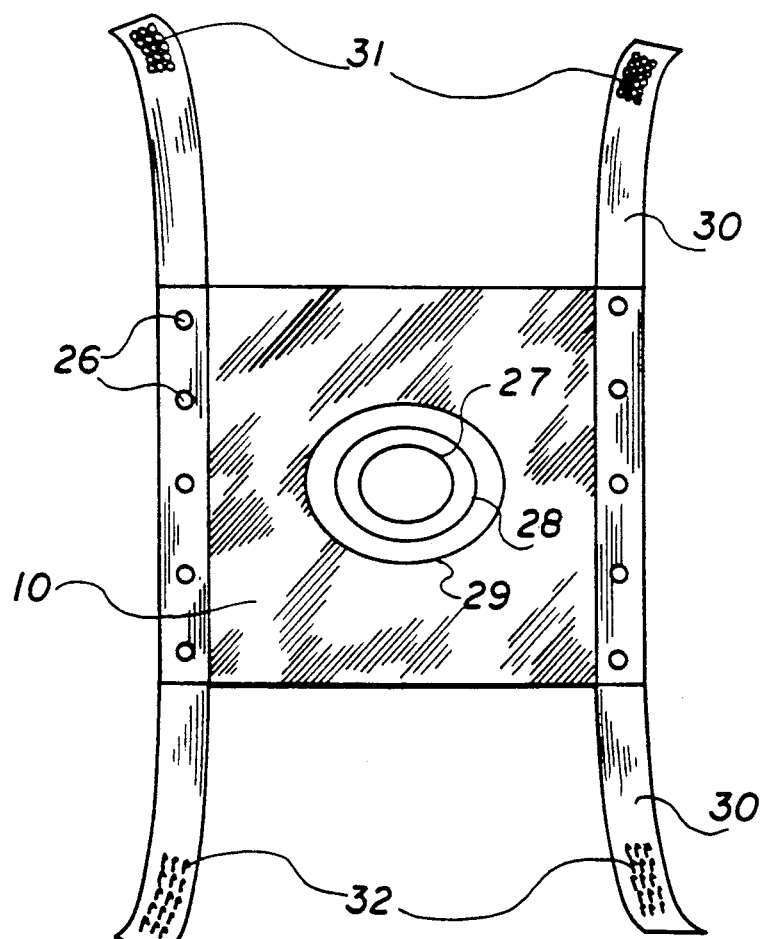
FIG. 5 is an elevation of a shield for patient use having pre-cut operative openings.

It is useful in a number of applications of the present invention to include eyelets 26 as shown in FIG. 5 along portions of the periphery of shield 10, as the use of eyelets permits the shield to be strategically placed in the laser operating environment to isolate the laser and its beam from personnel and/or equipment. Other forms of fasteners or hangers can be used to achieve the same purpose of tying or otherwise affixing shield 10 in position.

Another variation of shield 10 is shown in FIG. 5, in which pre-cut perforations 27, 28 and 29 are provided. Preferably, perforations are concentrically arranged circles or ellipses which the surgeon can remove to expose an operating field on the patient's body. Removing the innermost area 27, intermediate area 28, and outermost area 29 exposes an increasingly larger field in which to operate. Where the shield is to be used to protect a patient during laser surgery, it is desirable to include on the side facing the patient an adhesive to prevent movement of shield during the operative procedure. Further, in some surgical procedures, it may be preferable to utilize only one sheet of foil rather than a shield with multiple metallic layers as described above, that is, the foil is positioned only on the side exposed to the laser beam.

Also with reference to FIG. 5, shield 10 may also be formed in a sheath configuration for protection of personnel and equipment. Preferably, shield 10 includes at its distal and proximal sides or straps 30, loop 31 and hook 32 fastener strips. Straps 30 permit shield 10 to protect an area while at the same time permitting shield 10 to slide along the length of the surface to which shield 10 is attached, to permit the area being protected to be viewed. This variation is particularly useful when the protected areas are anesthesia circuits and equipment, in which the operator must have ready access to the protected area. In this embodiment, strips 31 and 32 are provided to attach the peripheral edges of shield 10 together. By use of such strips, equipment can be easily viewed by laser operating personnel who can easily open and then re-close the shield as needed during laser use operations.

Similarly, adhesive-backed shield "patches" of varying sizes, preferably of a different non-reflective color than the underlying primary shield to which it is to be applied, can be used to cover areas already damaged by laser impingement. In this sense, shields, drapes and eye masks can be restored to reestablish or improve protection of an area previously exposed to errant laser radiation, as well as to serve as a reminder to laser operating personnel of prior problem areas while avoiding the risk of leaving these areas inadequately protected.

While presently preferred embodiments of practicing the invention have been shown and described with particularity in connection with the accompanying drawings, the invention may otherwise be embodied within the scope of the following claims.

What is claimed is:

1. A laser shield for use during laser procedures comprising:
    a flexible insulating layer;
    a first flexible metallic layer positioned adjacent to the insulating layer;
    a flexible opaque layer applied to the surface of the metallic layer so as to coextensively interpose the metallic layer between the insulating layer and the opaque layer;
    a second flexible metallic layer positioned adjacent to and secured to the insulating layer so as to coextensively interpose the insulating layer between the metallic layers; and
    a securing means for attaching the opaque layer, the first and second metallic layer and insulating layer together.

2. A laser shield for use during laser procedures as set forth in claim 1, wherein the insulating layer is comprised of a laser-reactive material that will deteriorate to permit the metallic layers to physically touch, thereby changing the electrical current resistive properties between the metallic layers when the laser shield is exposed to laser radiation.

3. A laser shield for use during laser procedures as set forth in claim 1, wherein the insulating layer is comprised of a laser-reactive material that will change the electrical current resistive properties between the metallic layers when the laser shield is exposed to laser radiation.

4. A laser shield for use during laser procedures as set forth in claim 1, additionally comprising:
    a second flexible, opaque layer applied to and secured to the surface of the second the metallic layer opposite the surface adjacent to the insulating layer.

5. A laser shield as described in claim 1, wherein the flexible opaque layer is comprised of a laser-reactive material that will emit a puff of non-toxic smoke when the exterior opaque layer is exposed to laser radiation.

6. A laser shield as described in claim 1, wherein the exterior opaque layer is comprised of a laser-reactive material that will emit a popping sound when the flexible opaque layer is exposed to laser radiation.

7. A laser shield as described in claim 1, wherein the flexible opaque layer is comprised of a laser-reactive material that will react to when exposed to laser radiation by emitting a detectable odor.

8. A laser shield as described in claim 1, wherein the flexible opaque layer is comprised of a laser-reactive material that will bubble when exposed to laser radiation.

9. A laser shield as described in claim 1, wherein the insulating layer is comprised of a material threaded there through with a continuous strand of laser-reactive, electrically conductive wire, wherein the wire will melt so as to change the electrical current resistive properties of the wire.

10. A laser shield as described in claim 1, wherein the opaque layer is comprised of a material threaded therethrough with a continuous strand of laser-reactive, electrically conductive wire, wherein the wire will melt so as to change the electrical current resistive properties of the wire.

11. A laser shield as described in claim 1, wherein the insulating layer is comprised of an expandable laser-reactive material threaded therethrough with a continuous strand of electrically conductive wire, wherein the wire will be severed by expansion of the laser-reactive material when the laser shield is damaged or is subjected to laser radiation so as to change the electrical current resistive properties of the wire.

12. A laser shield for use during laser procedures comprising:
    a flexible insulating layer, wherein the insulating layer is comprised of a honeycomb structure of pockets containing an insulating material;
    a flexible metallic layer positioned adjacent to the insulating layer;
    a flexible opaque layer applied to the surface of the metallic layer so as to coextensively interpose the metallic layer between the insulating layer and the opaque layer; and
    a securing means for attaching the opaque layer, metallic layer and insulating layer together.

13. A laser shield as described in claim 1, wherein the shield is formed into a surgical eye mask for use during laser procedure, said surgical eye mask capable of conforming to the facial area of a wearer so as to protect the eyes of the wearer from laser energy.

14. A laser shield as described in claim 1, wherein the shield includes a means for fastening the shield to personnel and equipment consisting of a plurality of eyelets positioned around the periphery of the shield for fastening the shield to personel and equipment.

15. A laser shield as described in claim 1, wherein the shield includes hook and loop fastener strips for fastening the shield to personnel and equipment.

* * * * *